United States Patent
Duquette et al.

(10) Patent No.: US 7,509,957 B2
(45) Date of Patent: Mar. 31, 2009

(54) HARDWARE CONFIGURATION FOR PRESSURE DRIVER

(75) Inventors: Steven Duquette, Laguna Niguel, CA (US); Terry Blansfield, Orange, CA (US); Steve Han, Upland, CA (US); Harold Miller, Upland, CA (US)

(73) Assignee: Viasys Manufacturing, Inc., Conshohocken, PA (US)

( * ) Notice: Subject to any disclaimer, the term of this patent is extended or adjusted under 35 U.S.C. 154(b) by 270 days.

(21) Appl. No.: 11/358,420

(22) Filed: Feb. 21, 2006

(65) Prior Publication Data

US 2007/0193579 A1    Aug. 23, 2007

(51) Int. Cl.
*A62B 7/02* (2006.01)

(52) U.S. Cl. .............. 128/204.21; 128/204.26; 128/205.24

(58) Field of Classification Search ............ 128/202.22, 128/203.14, 203.24, 204.18, 204.21, 204.23, 128/204.25, 205.23, 205.24, 200.24, 204.24, 128/204.28, 207.14, 207.16; 604/23, 26
See application file for complete search history.

(56) References Cited

U.S. PATENT DOCUMENTS

| | | | |
|---|---|---|---|
| 2,985,357 A | | 5/1961 | Carolan |
| 3,630,196 A | | 12/1971 | Bird |
| 3,993,081 A | | 11/1976 | Cussell |
| 4,011,866 A | * | 3/1977 | Klein et al. ............ 128/204.21 |
| 4,018,221 A | | 4/1977 | Rennie |
| 4,098,290 A | | 7/1978 | Glenn |
| 4,261,355 A | | 4/1981 | Glazener |
| 4,281,641 A | * | 8/1981 | Devore ................. 126/605 |
| 4,282,869 A | | 8/1981 | Zisulka |
| 4,357,936 A | * | 11/1982 | Ellestad et al. ......... 128/204.23 |
| 4,457,304 A | * | 7/1984 | Molnar et al. ........... 128/204.25 |
| 4,459,982 A | * | 7/1984 | Fry ....................... 128/204.23 |
| 4,495,946 A | | 1/1985 | Lemer |
| 4,537,188 A | | 8/1985 | Phuc |
| 4,681,100 A | | 7/1987 | Brychta et al. |
| 4,782,832 A | | 11/1988 | Trimble et al. |
| 4,796,617 A | | 1/1989 | Matthews et al. |
| 4,915,105 A | | 4/1990 | Lee |
| 4,919,128 A | | 4/1990 | Kopala et al. |

(Continued)

FOREIGN PATENT DOCUMENTS

| | | |
|---|---|---|
| DE | 3119814 | 12/1982 |

OTHER PUBLICATIONS

International Search Report dated May 13, 2008, 2 pages.

*Primary Examiner*—Danton DeMille
(74) *Attorney, Agent, or Firm*—Baker & Hostetler LLP

(57) ABSTRACT

A pressure driver for a ventilation system comprises a gas source, an inspiration flow control valve and a patient pressure sensor to form a closed loop control system. The inspiration flow control valve may be mounted within a housing and is operative to open and close in response to patient pressure measurements in order to produce a desired pressure at the patient. The pressure driver may further include a mixture control for allowing selective adjustment of the oxygen concentration in pressurized gas delivered to the patient. An oxygen mixer is connected between the gas source and the mixture control and is operative to deliver the desired mixture of oxygen and air to the inspiration flow control valve for delivery to the patient. An oxygen sensor monitors the oxygen concentration in the gas provided by the oxygen mixer.

20 Claims, 5 Drawing Sheets

U.S. PATENT DOCUMENTS

| | | |
|---|---|---|
| 5,000,173 A | 3/1991 | Zalkin et al. |
| 5,113,857 A | 5/1992 | Dickerman et al. |
| 5,193,532 A | 3/1993 | Moa et al. |
| 5,259,376 A | 11/1993 | Bales |
| 5,477,852 A | 12/1995 | Landis et al. |
| 5,499,616 A | 3/1996 | Enright |
| 5,542,415 A * | 8/1996 | Brody .................... 128/204.23 |
| 5,752,510 A | 5/1998 | Goldstein |
| 5,829,428 A * | 11/1998 | Walters et al. ......... 128/200.24 |
| 5,865,174 A | 2/1999 | Kloeppel |
| 5,954,051 A * | 9/1999 | Heinonen et al. ...... 128/205.24 |
| 6,041,777 A * | 3/2000 | Faithfull et al. ........ 128/200.24 |
| 6,131,571 A * | 10/2000 | Lampotang et al. .... 128/204.21 |
| 6,412,483 B1 * | 7/2002 | Jones et al. ............ 128/205.11 |
| 6,431,172 B1 | 8/2002 | Bordewick |
| 2002/0104537 A1 * | 8/2002 | Banner et al. .......... 128/204.25 |
| 2003/0200970 A1 | 10/2003 | Stenzler |
| 2005/0150493 A1 | 7/2005 | Foster et al. |

* cited by examiner

HARDWARE CONFIGURATION FOR PRESSURE DRIVER

CROSS-REFERENCE TO RELATED APPLICATIONS (Not Applicable)

STATEMENT RE: FEDERALLY SPONSORED RESEARCH/DEVELOPMENT (Not Applicable)

BACKGROUND

The present invention relates generally to breathing apparatus and, more particularly, to a pressure driver for a continuous positive airway pressure (CPAP) ventilation system that utilizes pressure measurements in a closed loop control system for maintaining pressure at the patient. The pressure driver may be used in conjunction with a flow generator device to minimize exhalation resistance and reduce the work of breathing.

The use of breathing devices upon respiratory-impaired patients is well known. Generally, such devices assist in patient breathing by allowing the proper exchange of inhaled and exhaled gases while providing positive pressure to the patient's lungs throughout the respiratory cycle in order to prevent lung collapse. Ideally, such devices provide stable CPAP at the patient to facilitate the restoration of functional residual capacity (FRC) and reverse hypoxemia by recruiting collapsed alveoli.

Such breathing devices have proven to be effective in treating patients whose ability to breathe is impaired. For example, babies born with lung disease or premature neonates unable to maintain FRC may benefit from ventilatory support using CPAP therapy. As was earlier mentioned, CPAP therapy delivers a constant stable pressure to the mouth, nose or via a tracheal tube inserted into the infant. Although the use of such breathing devices have generally proven to be suitable for their intended purposes, such devices possess certain design deficiencies which detract from their overall clinical effectiveness in providing respiratory care.

For example, ventilator devices for infants can provide optimal CPAP treatment when delivering a constant and stable pressure to the patient airway. To accomplish this, such ventilator systems typically include a pressure driver for creating a flow of pressurized gas to the patient. The gas is delivered to a patient circuit which comprises the interface between the ventilator and the patient. A valve is typically provided between the gas source and the patient to control the pressure and/or flow of gas delivered to the patient.

Certain prior art infant ventilator devices utilize a manual flow control valve in order to control pressure at the patient. Unfortunately, variations in pressure may occur during CPAP therapy. Such pressure variations may be the result of leakage occurring in the ventilation system. For example, for infant ventilators using a patient interface configured with nostril-engaging stems, leaks may develop over time between the nostril-engaging stems and the infant's nose. If the patient interface is configured as a nasal mask covering the mouth and/or nose, leaks may also occur due to improper fitment of the mask to the patient's face or due to slippage of the mask during ventilation.

Unfortunately, because of the non-adjustable nature of manual flow control valves as used in prior art infant ventilator devices, such leakage in the ventilation system may go undetected and may result in a loss in pressure at the patient. Additionally, many infant ventilator devices of the prior art lack the capability for detecting leakage or detecting disconnections at the patient circuit. Furthermore, infant ventilator devices of the prior art lack the means for correcting for pressure losses at the patient as a result of such leakage and/or disconnections.

As can be seen, there exists a need in the art for a ventilation system that continuously monitors pressure at the patient for feedback to the pressure control mechanism such that accurate and stable positive pressure may be applied at the patient airway. Furthermore, there exists a need in the art for a ventilation system having the capability to detect system leakage and/or patient circuit disconnection such that the ventilation system may compensate for such leakage and thereby deliver the desired pressure to the patient.

BRIEF SUMMARY

The present invention specifically addresses the above referenced-needs associated with CPAP ventilation systems of the prior art. More specifically, in one aspect of the invention, a pressure driver is provided such as may be used for delivering continuous positive airway pressure (CPAP) ventilation to a patient. Advantageously, the pressure driver incorporates a patient pressure sensor disposed adjacent to the patient and which continually monitors pressure thereat for feedback to an inspiration flow control valve which is responsive thereto for accurately controlling CPAP in a stable manner.

The ventilation system may include a flow generator or micro generator patient circuit which may be used in conjunction with the pressure driver. Such flow generator may be similar to that which is shown and illustrated in U.S. patent application Ser. No. 11/241,303, filed Sep. 30, 2005 by Duquette et al. and which is entitled, Venturi Geometry Design for Flow Generator Patient Circuit, the entire contents of which is expressly incorporated by reference herein. Furthermore, such flow generator may include a nose piece member having anatomically-shaped nostril stems for reducing leakage at the patient interface. Such nose piece member may be similar to that shown and disclosed in U.S. Patent Application Publication No. 2003/0200970, filed Oct. 30, 2003 by Stenzler et al. and which is entitled Infant Breathing Apparatus, the entire contents of which is expressly incorporated by reference herein.

As was earlier mentioned, the closed loop control system for the pressure driver is specifically adapted to provide and maintain pressure at the patient. In this regard, the pressure driver utilizes patient pressure feedback at the inspiration flow control valve in order to produce a desired pressure at the patient. The inspiration flow control valve may be configured in a variety of valve configurations and preferably may be configured as a voltage sensitive orifice (VSO) valve which may be responsive to DC current or pulse width modulation.

Pressurized gas is provided via a gas source. A gas mixer may further be included in the pneumatic circuit to provide a mixture of oxygen and air to the inspiration flow control valve. A pressure regulator may be further incorporated into the pneumatic circuit in order to maintain a maximum pressure for delivery to the inspiration flow control valve. The oxygen concentration level in the gas may be selectively manipulated via a mixture control which may be configured as a rotatable knob or other suitable adjustment mechanism.

The mixture control may be configured to provide oxygen gas at any concentration ranging from zero percent to 100 percent as measured by an oxygen sensor that may also be incorporated into the pneumatic circuit. In CPAP treatment, the mixture control may be periodically adjusted in order to gradually reduce patient dependency upon the oxygen concentration as the patient acquires normal respiratory function.

Importantly, the patient pressure sensor is disposed adjacent the patient airway such as adjacent the patient wye port. The patient pressure sensor may be configured as a pressure transducer or other suitable instrument for measuring pressure in gas delivered to the patient. The inspiration flow control valve is responsive to such patient pressure measurements. A processor may also be included in the closed loop control system and which operates in accordance with a preprogrammed or manually-set desired patient pressure level.

An inspiratory check valve may be further included in the pneumatic circuit and is preferably operative to block the flow of pressurized gas in a direction toward the inspiration flow control valve. A safety valve may be also incorporated into the pneumatic circuit and may cooperate with the inspiratory check valve as a secondary safety feature for ventilating the patient in the event of a malfunction of the ventilation system. In this manner, the patient may receive adequate ventilation despite loss of gas flow from the inspiration flow control valve.

The desired patient pressure may be selectively manipulated or adjusted by any suitable means such as via a pair of push buttons mounted on the pressure driver housing. Readouts of desired patient pressure and actual patient pressure may also be provided in the form of LED elements disposed on the pressure driver housing. As was earlier mentioned, manipulation of the oxygen concentration in the gas flow to the patient may be provided by means of a mixture control configured as a rotatable knob mounted on the pressure driver housing.

An oxygen sensor incorporated into the pneumatic circuit provides a means for monitoring the concentration of oxygen in the gas. The oxygen concentration level may be displayed such as via a digital readout device using a set of LED elements. A proximal pressure sensor may further be provided in the pneumatic circuit in order to monitor and detect leakage within the ventilation system as well as for detecting disconnects.

BRIEF DESCRIPTION OF THE DRAWINGS

These and other features and advantages of the various embodiments disclosed herein will be better understood with respect to the following description and drawings in which like numbers refer to like parts throughout and in which.

DETAILED DESCRIPTION

Figure 1:
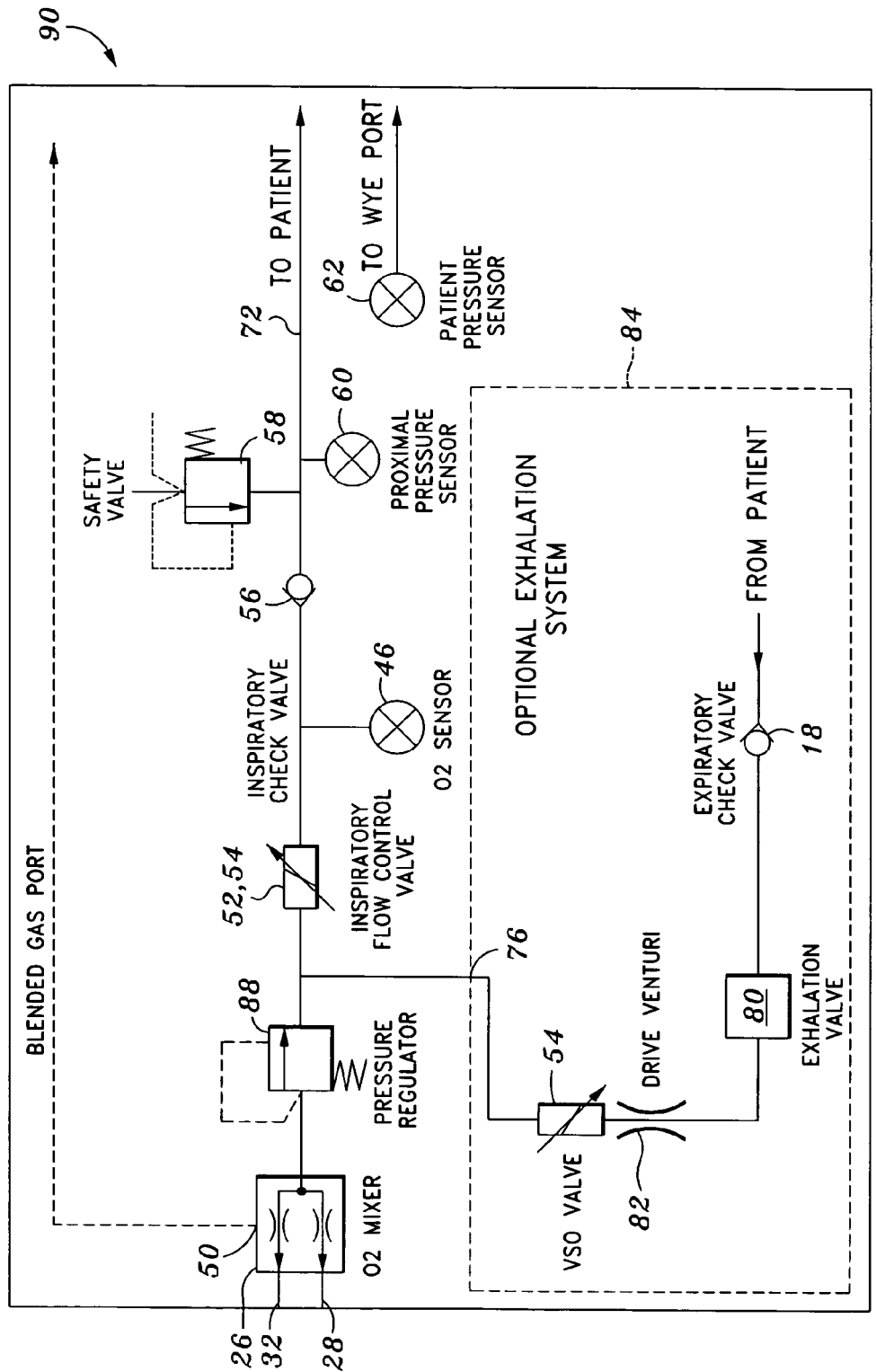
FIG. 1 is a pneumatic diagram of a ventilation system and pressure driver such as may be used for providing CPAP therapy to a patient.

Referring now to the drawings wherein the showings are for purposes of illustrating preferred embodiments of the present invention only, and not for purposes of limiting the same, FIG. 1 is a pneumatic diagram of a ventilation system as may be used for providing continuous positive airway pressure (CPAP) therapy to a patient. The ventilation system includes a pressure driver 10 for providing pressurized gas to the patient. Although not shown in FIG. 1, the ventilation system may also include a flow generator or micro generator (not shown) patient circuit such as that which is disclosed in U.S. patent application Ser. No. 11/241,303, filed Sep. 30, 2005 by Duquette et al. and which is entitled, Venturi Geometry Design for Flow-Generator Patient Circuit, the entire contents of which is expressly incorporated by reference herein.

As was mentioned above, the flow generator may be useful in facilitating inhalation and exhalation during CPAP treatment. In this regard, the pressure driver 10 may be utilized in conjunction with the flow generator to provide a stable CPAP pressure in order to facilitate restoration of functional residual capacity (FRC) of the patient and to correct hypoxemia. Such flow generator is typically installed at the patient interface and may include a nose piece member having D-shaped nostril-engaging stems that anatomically conform to the patient's nostrils such as is disclosed and shown in U.S. Patent Application Publication No. 2003/0200970, filed Oct. 30, 2003 by Stenzler et al. and which is entitled, Infant Breathing Assist Apparatus, the entire contents of which is expressly incorporated by reference herein. As can also be seen in FIG. 1, the ventilation system may optionally include an exhalation system 84 to facilitate removal of exhalation gases from the patient.

Importantly, the pneumatic system includes a closed loop control system 72 for the pressure driver 10 in order to maintain pressure at the patient. In this regard, the pressure driver 10 utilizes patient pressure for feedback to an inspiration flow control valve 52 in order to provide accurate and stable positive airway pressure. The inspiration flow control valve 52 is operative to open and close in response to patient pressure measurement in order to produce a desired pressure at the patient.

As can be seen in the pneumatic diagram of FIG. 1, the gas source 26 is preferably operative to deliver a mixture of oxygen and air to the inspiration flow control valve 52. The air may be drawn by the gas source 26 from ambient atmosphere after which the air may be mixed with oxygen and/or other gases or combinations thereof for delivery to the patient. The air may also be drawn from the environment or from a compressed air tank or other suitable source. Likewise, the oxygen may be drawn from an oxygen tank or other suitable source. It is also contemplated that oxygen may be delivered downstream of the gas source 26 such as downstream of the inspiration flow control valve 52 or at the patient interface and may be regulated to control the concentration of oxygen delivered to the patient.

As can be seen in FIG. 1, the patient pressure sensor 62 may be disposed adjacent a patient wye. The patient pressure sensor 62 may be configured as a pressure transducer or other suitable instrument for measuring pressure in gas delivered to the patient. The inspiration flow control valve 52 is generally located between the gas source 26 and the patient and is operative to open and close in response to patient pressure measurements. In this regard, the patient pressure sensor 62 and the inspiration flow control valve 52 comprise the closed loop control system 72. The closed loop control system 72 may further include a processor or microprocessor adapted to generate a control system command in response to the patient pressure measurements. Such control system command is then delivered to the inspiration flow control valve 52 which is operative to produce the desired pressure at the patient. User input capability and memory capability may be included in the control system, as described in greater detail below.

As can be seen in FIG. 1, the pneumatic circuit may further include a proximal pressure sensor 60 which may be disposed internally to the pressure driver 10 and which is preferably operative to detect leakage in the ventilation system. Like the patient pressure sensor 62, the proximal pressure sensor 60 may be configured as a pressure transducer and is preferably operative to continuously sample pressure in the ventilation system for feedback to the closed loop control system 72. In this manner, leakage within the ventilation system or at the patient interface may be detected such that the inspiration flow control valve 52 may make the appropriate corrections such that pressure may be maintained at the patient.

A pressure regulator 88 is also preferably incorporated into the pressure driver 10. As shown in FIG. 1, the pressure driver 10 is fluidly connected between the gas source 26 and the inspiration flow control valve 52 and is preferably operative to regulate the pressure of gas flowing from the gas source 26 and/or from an oxygen mixer 86 disposed downstream of the gas source 26. The pressure regulator 88 ensures that a constant source of pressurized gas is made available to the inspiration flow control valve 52.

As was earlier mentioned, the inspiration flow control valve 52 is responsive to feedback from the patient pressure sensor 62 and opens and closes the appropriate amount in accordance with a preprogrammed or manually-set desired patient pressure level. The inspiration flow control valve 52 may be configured as a voltage sensitive orifice (VSO) valve 54 although alterative valve configurations may be used for the inspiration flow control valve 52. In the VSO configurations, the inspiration flow control valve 52 is a solenoid valve that is responsive to open and close in proportion to DC current or pulse width modulation under the closed loop control system 72. In this manner, the VSO valve 54 may control the flow of pressurized gas in the pneumatic circuit in proportion to input current.

As was earlier mentioned, the pressure driver 10 may include the oxygen mixer 86 which is operative to provide a mixture of ambient air and oxygen to the patient. In this regard, the pneumatic circuit preferably may include an oxygen sensor 46 disposed downstream of the inspiration flow control valve 52. The oxygen sensor 46 is preferably operative to measure the concentration of oxygen in the pressurized gas that is being delivered to the patient. The oxygen concentration may be selectively adjusted via an oxygen mixture control 44 mounted on the pressure driver 10, as will be described below in the pressure driver 10 hardware description. In CPAP treatment, the mixture control 44 may be periodically adjusted in order to gradually reduce patient dependency upon the oxygen concentration in the pressurized gas as the patient acquires normal respiratory function. The mixture control 44 may be configured to provide oxygenated gas at any percentage ranging from zero percent to 100 percent as measured by the oxygen sensor 46.

An inspiratory check valve 56 may be further included in the pneumatic circuit as shown in FIG. 1. The inspiratory check valve 56 may be interposed between the patient and the inspiration flow control valve 52 and is preferably operative to block the flow of pressurized gas in a direction from the patient toward the inspiration flow control valve 52. In this regard, the inspiratory check valve 56 allows flow in a single direction only (i.e., toward the patient). As shown in the pneumatic circuit, a safety valve 58 may be located between the patient and inspiratory check valve 56. The safety valve 58 cooperates with the inspiratory check valve 56 to provide a secondary safety feature for ventilation of the patient in the event of a malfunction of the ventilation system such that the patient may receive appropriate ventilation despite a malfunction of the ventilation system.

As was earlier mentioned, the closed loop control system 72 for the pressure driver 10 provides accurate and stable pressure at the patient airway despite changes in the pneumatic circuit or changes at the patient circuit. Signals from the patient pressure sensor 62 may also be converted to a visual and/or audible format for pressure indication such that a clinician may observe and monitor actual patient pressure. In this regard, a desired patient pressure indicator 66 and an actual patient pressure indicator 68 may be provided in digital readout format. A patient pressure control 64 mechanism may further be included with the hardware configuration of the pressure driver 10 as a means to allow selective adjustment of the desired patient pressure. More specifically, the desired patient pressure may be selectively manipulated via a pair of push buttons mounted on a housing 12 of the pressure driver 10.

Referring still to the pneumatic diagram of FIG. 1, the ventilation system may optionally further include an exhalation system 84 for facilitating discharge of exhalation gases from the patient upon initiation by the patient. As can be seen, the exhalation system 84 may interconnect the patient to the gas source 26 at a location downstream of the pressure regulator 88. In this regard, pressurized gas is provided to the exhalation system 84 to facilitate removal of exhalation gases. The exhalation system 84 is arranged in parallel with the pressure driver 10 which delivers inspiration gases to the patient. The exhalation system 84 includes the required componentry to vent exhalation gases from the patient in a manner which reduces the work of breathing.

More specifically, the exhalation system 84 may include an expiratory check valve 78, an exhalation valve 80, a drive venturi 82 and a VSO valve 54. Similar to the operation of the inspiratory check valve 56, the expiratory check valve 78 allows only one-way flow therethrough. More particularly, the expiratory check valve 78 is configured to prevent flow of exhalation gases in a direction toward the patient. The exhalation valve 80 interconnects the expiratory check valve 78 to the patient and is preferably operative to vent exhalation gases from the patient. Such exhalation gases may be vented to the environment. The drive venturi 82 facilitates removal of exhalation gases upon initiation by the patient. Due to its unique geometry, gases readily flow from the exhalation valve 80 via the drive venturi 82.

Upon initiation of the exhalation phase by the patient, the drive venturi 82 promotes the exhaustion of exhalation gases out of the patient's airway. The VSO valve 54 is connected to the drive venturi 82 as shown in FIG. 1 and is also connected to the pressure driver 10 between the pressure regulator 88 and the inspiration flow control valve 52. The VSO valve 54 provides a regulated flow of pressurized gas to the drive venturi 82 for removal of exhalation gases in order to reduce the work of breathing. Also shown in the pneumatic circuit of FIG. 1 is an optional blended gas port 50 extending from the oxygen mixer 86. Such blended gas port 50 may be fluidly connected to supply pressurized gas to a closed exhalation valve 80 system such as may be used for dual-limb patient circuits.

Referring now to FIGS. 2-6, shown is an exemplary embodiment of a hardware configuration for the pressure driver 10 as utilized in the ventilation system shown in FIG. 1. The pressure driver 10 may include a housing 12 which may include a pair of feet 22 for supporting the pressure driver 10 on a countertop, table or stand. Although shown as being generally orthogonally shaped, the housing 12 may be configured in a wide variety of shapes, sizes and alternative configurations. The housing 12 may have a mounting plate 20 and front and back portions with the back portion serving as means for connection of the air port 32 and oxygen port 28. The back portion may further include a back plate 18 to which a manifold may be mounted for receiving the air and oxygen ports 32, 28.

Figure 3:
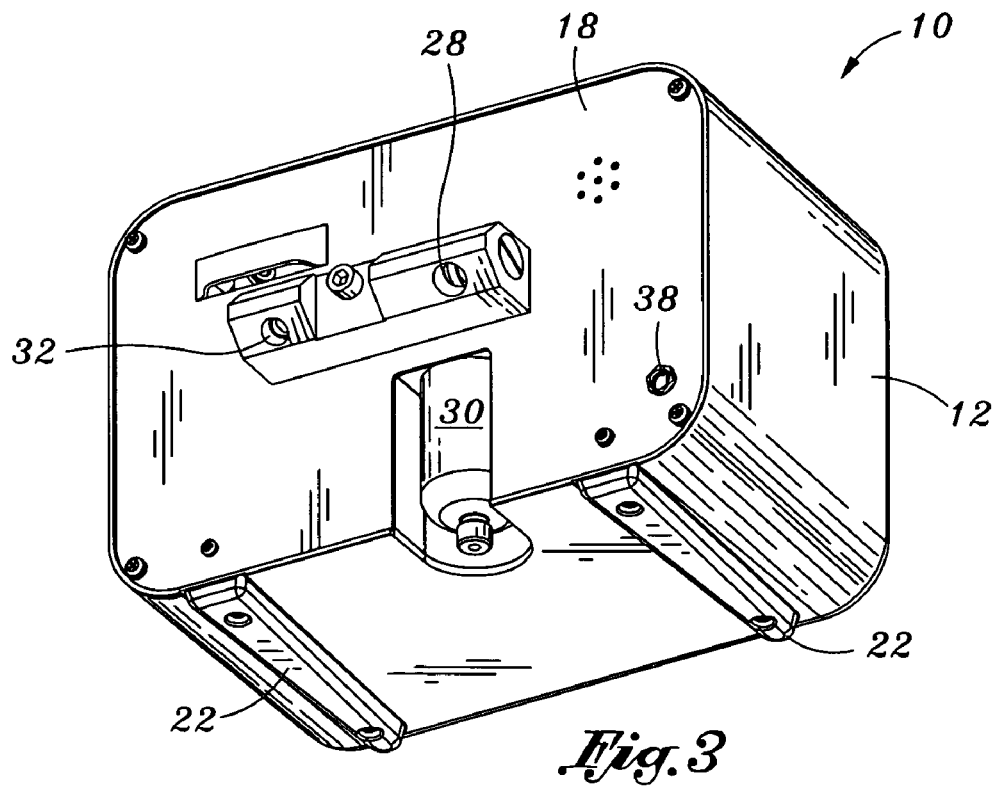
FIG. 3 is a perspective view of a rear portion of the pressure driver and illustrating an air port and an oxygen port which may collectively comprise a gas source for the ventilation system.
Figure 4:
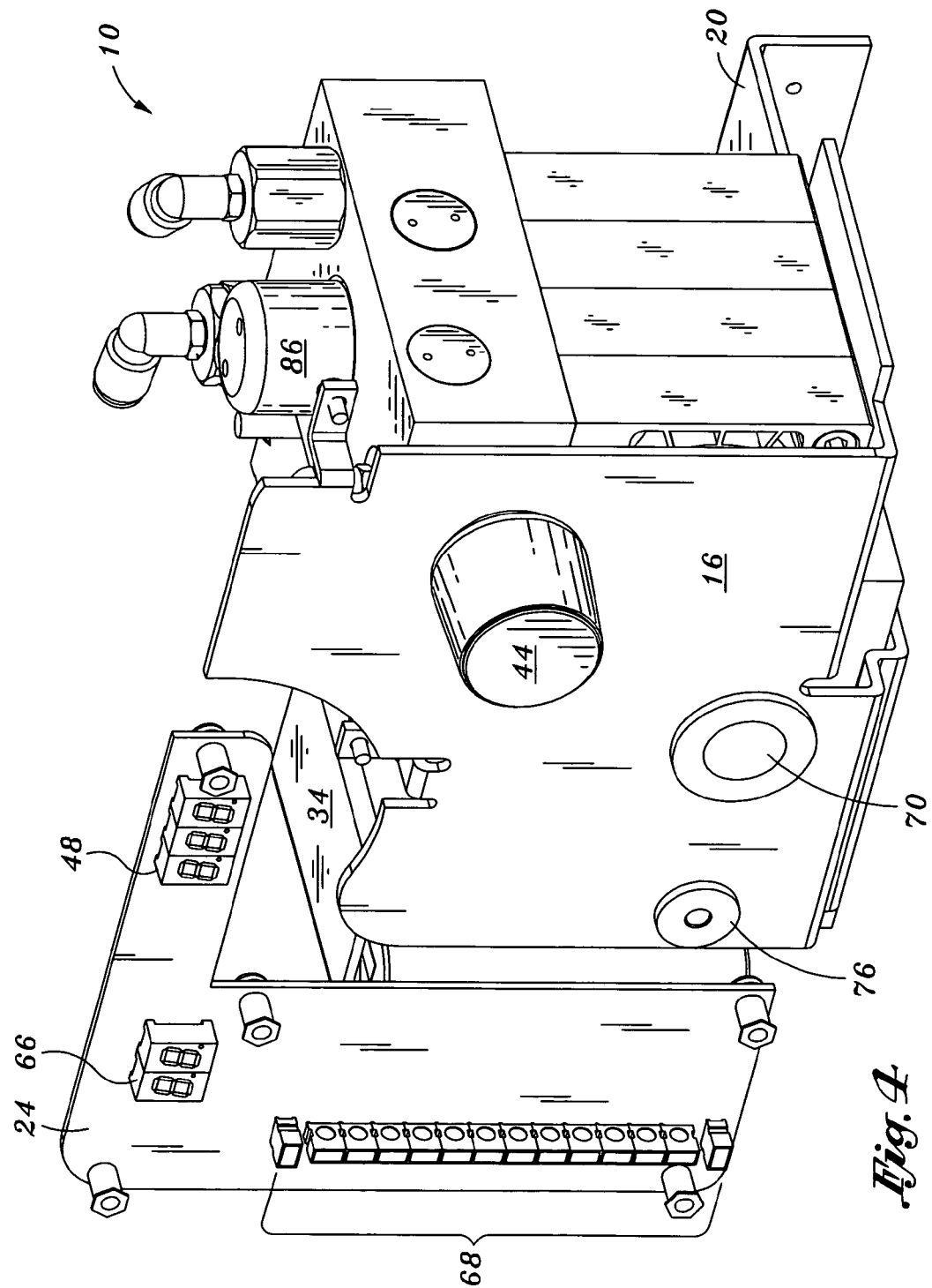
FIG. 4 is a perspective view of the pressure driver and illustrating an oxygen mixer for mixing ambient air and oxygen delivered by the air and oxygen ports, respectively.

A power supply port 38 may be disposed or mounted on the back plate 18. The power supply port 38 may be configured to supply power to the pressure driver 10 and/or to charge an internal battery 36 or battery pack 34. As can be seen in FIG. 3, the pressure driver 10 may further include a filter 30 which may be fluidly connected to the oxygen port 28 and which is preferably operative to filter oxygen flowing therefrom to a predetermined purity level such as, for example, to 0.5 microns. The filter 30 can also be seen in FIG. 5 and is disposed adjacent to the manifold through which oxygen flows. Once filtered, the oxygen is then provided to the oxygen mixer 86 also visible in FIG. 5.

Air from the air port 32 also flows to the oxygen mixer 86 whereupon the desired concentration of oxygen is mixed therewith and provided to the inspiration flow control valve 52 according to a predetermined or user-set concentration level. Such oxygen concentration is regulated by manipulation of the mixture control 44 which is shown as a rotatable knob extending from a face plate 16 on a front side of the housing 12.

As was earlier mentioned, the concentration of oxygen can be provided in any range from zero percent to 100 percent. A mixture indicator 48 is also provided on the face plate 16 of the housing 12 of the pressure driver 10. Illustrated in the figures as a three-digit digital readout device, the mixture indicator 48 may be configured in any suitable configuration for displaying the oxygen concentration of the pressurized gas as measured by the oxygen sensor 46.

Figure 5:
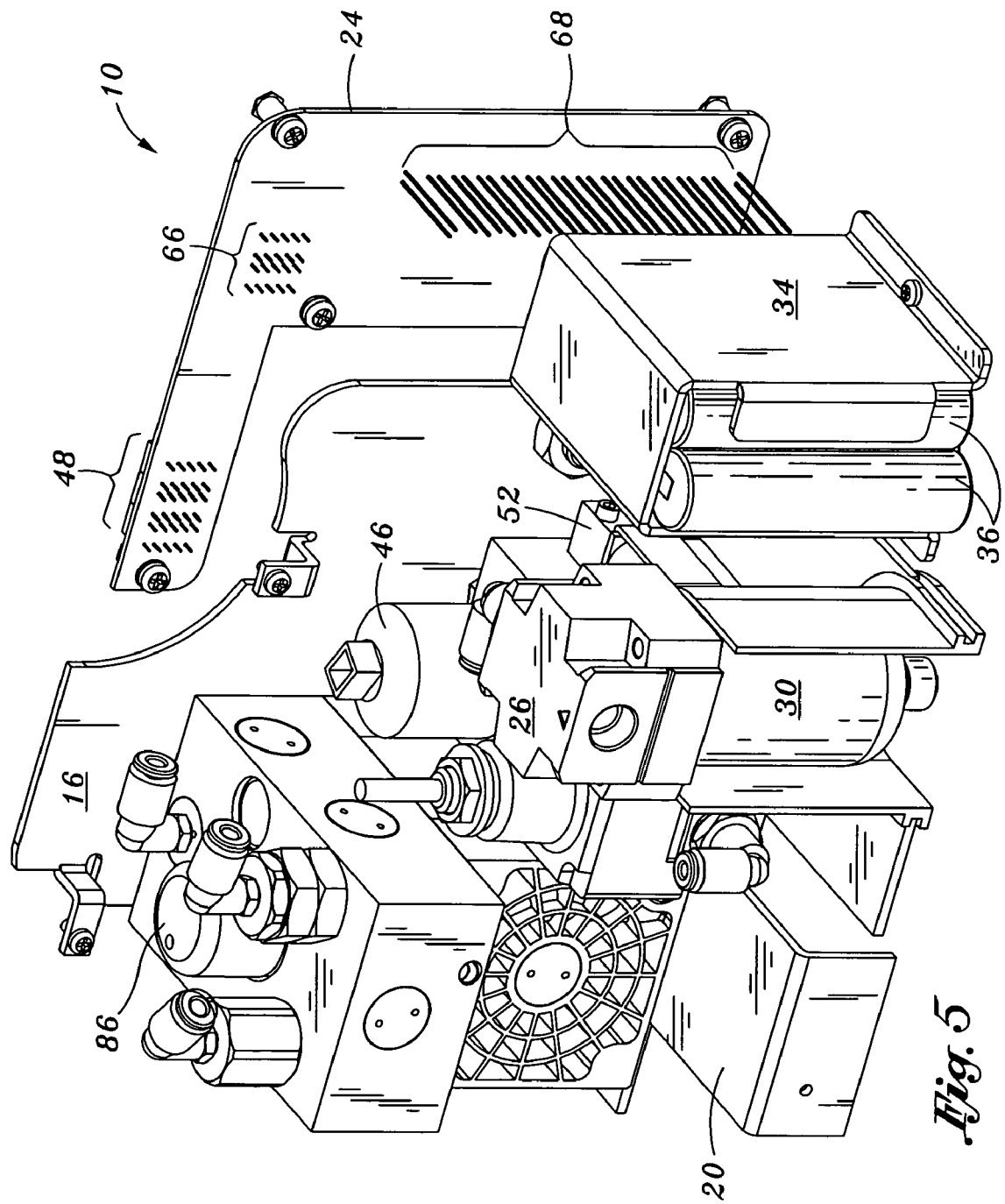
FIG. 5 is a perspective aft view of the pressure driver and illustrating the various components that make up the pressure driver.
Figure 6:
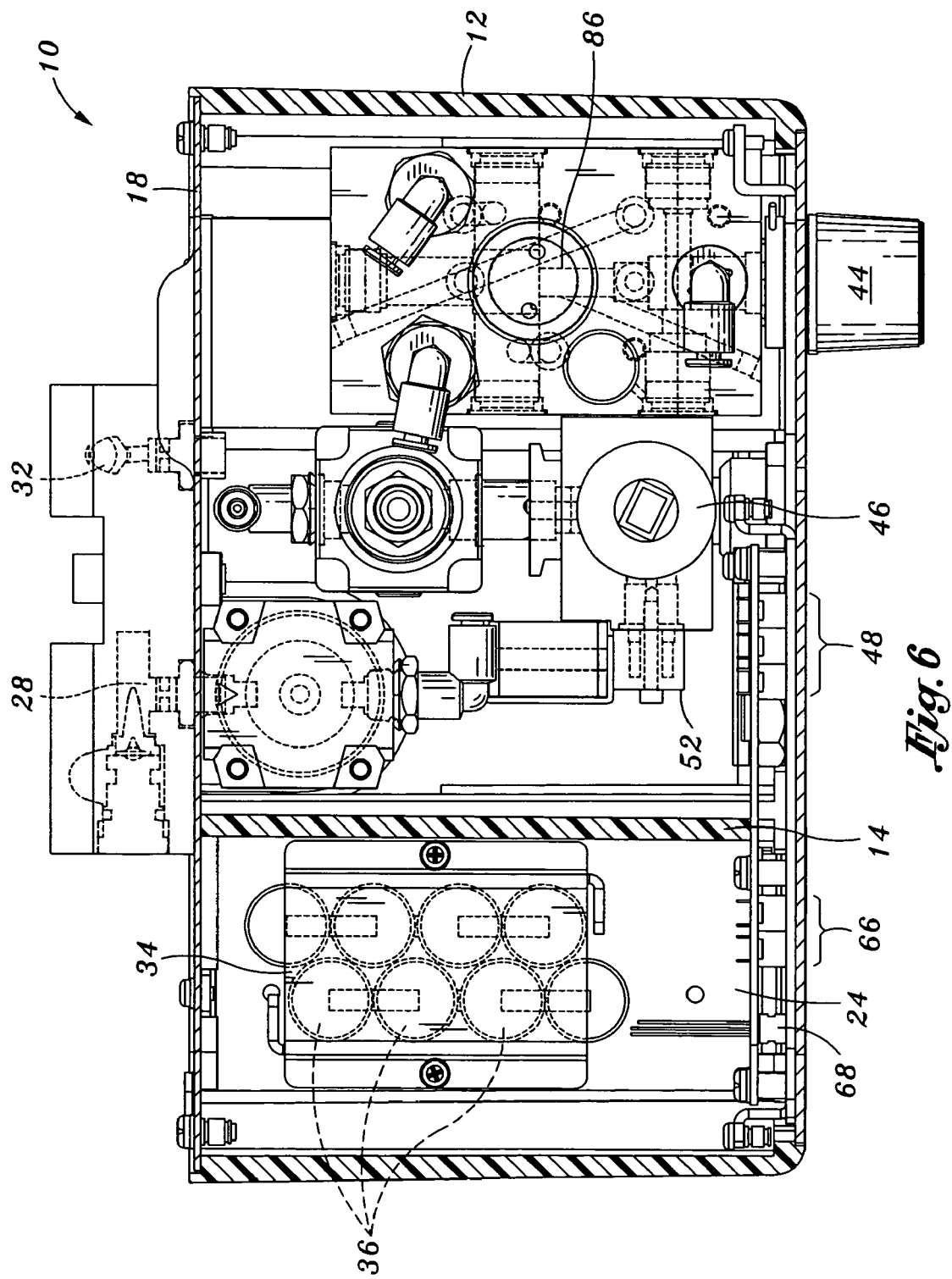
FIG. 6 is a cross-sectional top view of the pressure driver illustrating various components thereof including, but not limited to, a battery pack, the air and oxygen ports, the oxygen mixer, a mixture control, an oxygen sensor, a mixture indicator and an inspiratory flow control valve.

The pressure driver 10 further includes the patient pressure sensor 62 which is preferably disposed adjacent to or contained within the housing 12. The patient pressure sensor 62 is operative to measure pressure at the patient for feedback to the inspiration flow control valve 52. The inspiration flow control valve 52 can be seen mounted within the housing 12 as shown in FIGS. 5 and 6 and, as was earlier mentioned, is operative to open and close in response to feedback on the patient pressure measurement in an aspect of the present invention, the patient pressure sensor 62 is preferably disposed at the patient interface device.

The inspiration flow control valve 52 and the patient pressure sensor 62 are defined in the present application as comprising the closed loop control system 72. The closed loop control system 72 may include a processor capable of receiving input from the patient pressure sensor 62 and, based on signals produced thereby, perform necessary memory and processing functions in order to control the actuating parameters of the inspiration flow control valve 52. As was also earlier mentioned, the inspiration flow control valve 52 may be implemented as a VSO valve 54 although other valves types are contemplated.

Also disposed on the front portion of the pressure driver 10 is the desired patient pressure indicator 66 and actual patient pressure indicator 68. Similar to the configuration of the mixture indicator 48, the desired patient pressure indicator 66 may also be configured as a digital readout or digital display such as via light-emitting-diode (LED) type devices or other suitable display devices. Manipulation of the desired patient pressure may be effectuated through the use of a patient pressure control 64 which is also preferably disposed on the front portion of the pressure driver 10.

Figure 2:
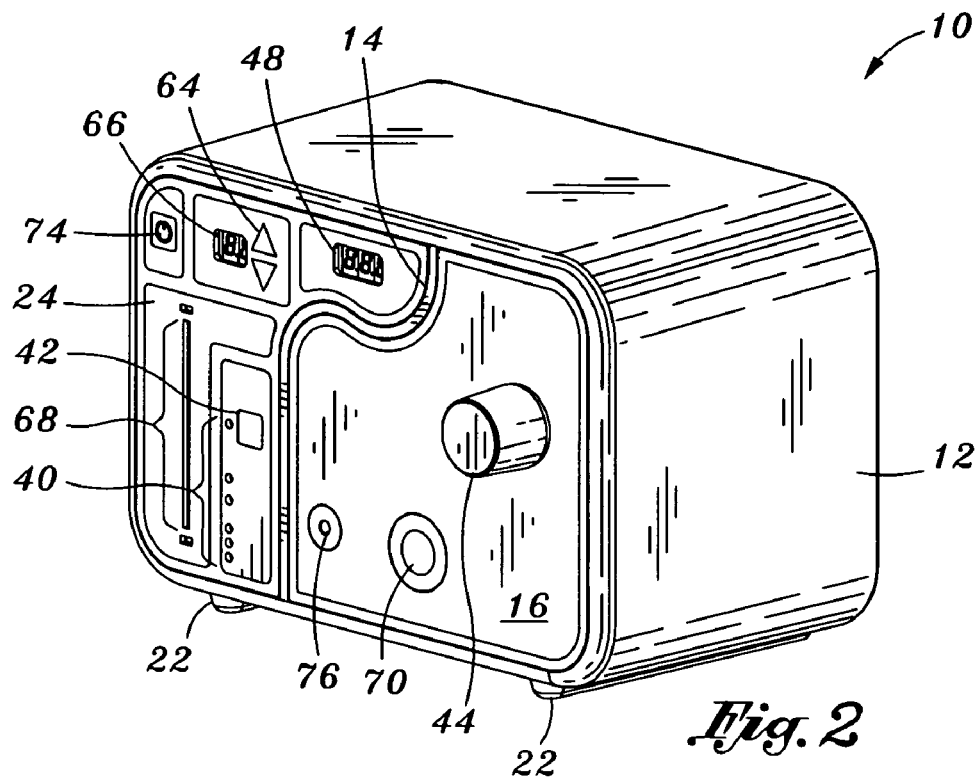
FIG. 2 is a perspective front view of the pressure driver as may be used in the ventilation system for providing pressurized gas to the patient.

As shown in FIG. 2, patient pressure control 64 may be configured as a pair of buttons shaped as arrows and which allow the user to increase or decrease the desired patient pressure. Alternatively, various other control means may be provided for the patient pressure control 64. The actual patient pressure indicator 68 may be configured as a bar graph manometer formed as a vertical array of LED's to indicate actual patient pressure as measured by the patient pressure sensor 62 as measured in cm. of $H_2O$. However, a digital readout or other suitable user interface is contemplated for providing an indication of the actual patient pressure. Mounted at the extreme upper and lower ends of the bar graph manometer for the actual patient pressure, a pair of high and low pressure alarm 42 settings (e.g., LED's) are preferably configured to respond to patient pressure measurement outside of a predetermined range as measured at the patient by the patient pressure sensor 62.

Activation of the pressure driver 10 may be facilitated by means of a power switch 74 which may be mounted on a front portion of the pressure driver 10. Power may be provided in AC via the power supply port 38 disposed on the rear portion of the pressure driver 10. As can be seen in FIG. 6, the pressure driver 10 may include a battery pack 34 comprised of at least one and, preferably, several batteries to power the pressure driver 10 during intra-hospital transport or ambulatory transport. In addition, the battery pack 34, which may be rechargeable, may also be configured to provide back-up power in the event of a power outage such that critical care respiratory support is provided at all times.

In order to provide status on power, a power indicator 40 display device may be disposed on a front portion of the pressure driver 10. The power indicator 40 is preferably configured to provide a readout regarding battery power level and other power conditions. For example, the power indicator 40 may comprise an array of LED bars and/or digital displays configured to indicate power 40 "On/Off" conditions as well as available battery charge and/or battery power levels. Furthermore, provisions for indicating whether power is provided via an AC source or from the battery pack 34 may also be available on the pressure driver 10 such as on the front potion thereof.

Each of the above-mentioned control and display mechanisms may be further provided with any variety of visual and/or audible alarm capabilities. For example, a high or low patient pressure reading as monitored by the patient pressure sensor 62 may activate a visual and/or audible alarm 42. Likewise, loss of battery power and/or AC power or a low power level condition may be indicated by means of an audible or visual alarm 42. It is also contemplated that such alarm 42 mechanisms are configured to be re-settable.

As shown in the figures, it is contemplated that the above-mentioned regulatory and monitoring devices (i.e., mixture indicator 48, desired patient pressure indicator 66 and actual patient pressure indicator 68) may be mounted on a printed circuit board 24 disposed on the front side of the housing 12 of the pressure driver 10. Likewise, patient supply port 70 and exhalation system port 76 may be mounted on the faceplate on the front portion of the housing 12 of the pressure driver 10.

It should be pointed out that the above-disclosed structural arrangement of the various pressure and oxygen regulatory and monitoring devices may be arranged in any suitable form other than that which is shown and described herein. The housing 12 itself may include a divider 14 member which may generally divide an internal compartment defined by the housing 12. The divider 14 may separate electrical components (i.e., battery pack 34, printed circuit board 24 with mixture indicator 48, desired patient pressure indicator 66 and actual patient pressure indicators 68 mounted thereon) from pneumatic elements such as the mixture control 44, patient supply port 70 and exhalation system port 76.

Referring to FIGS. 1-6, the operation of the pressure driver 10 will now be described. Upon fluid interconnection of the patient supply port 70 to the patient circuit such as via the appropriate patient interface, and with optional interconnection of the exhalation system 84 to the pressure driver 10 via the exhalation system port 76, the pressure driver 10 may be activated with the power switch 74. Oxygen may be provided via an oxygen tank or other suitable oxygen source through the oxygen port 28 at the rear portion of the housing 12.

The oxygen may be passed through the filter 30 shown in FIGS. 3 and 5 prior to delivery to the oxygen mixer 86. Air may be drawn into the air port 32 and is delivered to the oxygen mixer 86. The user may regulate the desired oxygen concentration by manipulating (i.e., rotating) the mixture control 44 located on the front portion of the pressure driver 10. The mixture of pressurized gas is then delivered to the pressure regulator 88 which limits the maximum pressure thereof. The pressurized gas is then provided to the inspiration flow control valve 52 which operates in response to user input regarding patient pressure.

As was earlier mentioned, the patient pressure control 64 may allow for selective manipulation of the pressure in the pneumatic circuit. The patient pressure sensor 62 continuously monitors pressure at the patient and delivers signals representative thereof to the inspiration flow control valve 52 which then opens and closes in order to achieve the desired patient pressure. The inspiratory check valve 56 prevents the flow of the gas in a direction from the patient to the inspiration flow control valve 52 and works in combination with the safety valve 58 as a secondary safety feature during patient ventilation. The proximal pressure transducer senses and detects pressure losses such as due to leakage at the patient interface or at other locations within the pneumatic circuit and sends representative signals thereof to the controller (i.e., to the control system) for compensating purposes.

The optional exhalation system 84 may be supplied with pressurized gas from the pressure regulator 88 and works in conjunction with the VSO valve 54 and drive venturi 82 to facilitate removal of the patient's exhalation gases through the exhalation valve. The expiratory check valve 78 is disposed between the exhalation valve and the patient and prevents flow from the exhalation valve back to the patient. User input regarding desired patient pressure may be effectuated by manipulating the pair of buttons as was earlier mentioned. Furthermore, oxygen concentration in the gas delivered to the patient may be regulated by manipulating (i.e., rotating) the mixture control 44 on the front portion of the pressure driver 10.

Visual and/or audible indications of the actual and desired patient pressures may be provided via the actual patient pressure indicator 68 and desired patient pressure indicator 66 which may be configured in any suitable form including the LED readouts mentioned above. It is contemplated that other input and output capability (e.g., memory capability and data input capability) may be incorporated into the control system of the pressure driver 10. Power status of the pressure driver 10 may likewise be communicated to a user via a power level and alarm 42 provision as mentioned above. Advantageously, the incorporation of the battery 36 and/or battery pack 34 allows for intra-hospital transport or for emergency back-up power in the event of a power outage.

Additional modifications and improvements of the present invention may also be apparent to those of ordinary skill in the art. Thus, the particular combination of parts described and illustrated herein is intended to represent only certain embodiments of the present invention and is not intended to serve as limitations of alternative devices within the spirit and scope of the invention.

What is claimed is:

1. A pressure driver for a ventilation system for ventilating a patient, the pressure driver comprising:
   a gas source;
   a drive venturi connected to the ventilation system;
   a patient pressure sensor operative to measure pressure at the drive venturi; and
   an inspiration flow control valve interposed between the gas source and the patient and being operative to open and close in response to patient pressure measurements; and
   an exhalation system interconnecting the patient to the gas source and being arranged in parallel with the inspiration flow control valve, the exhalation system being operative to vent exhalation gases from the patient, wherein the exhalation system includes an exhalation valve and an expiratory check valve interconnecting the exhalation valve to the patient, the expiratory check valve being operative to prevent flow in a direction from the exhalation valve to the patient and wherein the exhalation system includes the drive venturi interposed between a voltage sensitive orifice (VSO) valve and the exhalation valve, the drive venture being operative to facilitate the flow of gas.

2. The pressure driver of claim 1 wherein:
   the patient pressure sensor and the inspiration flow control valve comprise a closed loop control system operative to generate a control system command in response to the patient pressure measurements; and
   the inspiration flow control valve being operative to open and close in response to the control system command for producing a desired pressure delivered to the patient.

3. The pressure driver of claim 2 wherein the control system further includes a proximal pressure sensor operative to detect leakage at the patient.

4. The pressure driver of claim 1 wherein the patient pressure sensor is configured as a pressure transducer.

5. The pressure driver of claim 1 wherein the gas source is operative to deliver a mixture of oxygen and air to the inspiration flow control valve.

6. The pressure driver of claim 5 further including an oxygen sensor operative to measure the oxygen concentration in the gas delivered to the patient.

7. The pressure driver of claim 1 wherein the inspiration flow control valve is configured as a voltage sensitive orifice (VSO) valve.

8. The pressure driver of claim 1 further comprising a safety valve interposed between the patient and the inspiration flow control valve.

9. The pressure driver of claim 8 further comprising an inspiratory check valve interposed between the patient and the inspiration flow control valve and being operative to block the flow in a direction from the patient to the inspiration flow control valve.

10. A pressure driver for a continuous positive airway pressure (CPAP) ventilation system for ventilating a patient, the pressure driver comprising:
   a gas source;
   a pressure regulator fluidly connected to the gas source and being operative to regulate the pressure of gas from the gas source;
   a closed loop control system comprising:
      an inspiration flow control valve fluidly connected between the pressure regulator and the patient;
      a patient pressure sensor operative to measure pressure delivered to the patient for feedback to the inspiration flow control valve;
   an exhalation system extending from the patient in parallel with the inspiration flow control valve, the exhalation system including;
      an expiratory check valve configured to prevent flow in a direction toward the patient;
      an exhalation valve interconnecting the expiratory check valve to the patient and being operative to vent exhalation gas from the patient;
   a drive venturi connected to the exhalation valve and being configured to facilitate the flow of exhalation gas from the exhalation valve; and
   a voltage sensitive orifice (VSO) valve connected to the drive venturi and being interconnected between the pressure regulator and the inspiration flow control valve and being operative to regulate the flow of gases from the exhalation valve,
   wherein the inspiration flow control valve is operative to open and close in response to patient pressure measurements.

11. The pressure driver of claim 10 wherein the control system further includes a proximal pressure sensor operative to detect leakage at the patient.

12. The pressure driver of claim 10 wherein the gas source includes an oxygen mixer configured to provide a mixture of ambient air and oxygen to the patient.

13. The pressure driver of claim 10 wherein the control system further includes a proximal pressure sensor interposed between the patient and the inspiration flow control valve, the proximal pressure sensor being operative to detect leakage at the patient.

14. The pressure driver of claim 10 further comprising a safety valve interposed between the patient and the inspiration flow control valve and being operative to limit the pressure of gas delivered to the patient.

15. The pressure driver of claim 10 further comprising an inspiratory check valve interposed between the patient and the inspiration flow control valve and being operative to prevent flow in a direction from the patient to the inspiration flow control valve.

16. The pressure driver for a ventilation system for ventilating a patient, the pressure driver comprising:
   a housing
   a gas source comprising an oxygen port and an air port mounted on the housing;
   a patient pressure sensor disposed on the housing and being operative to measure pressure at a drive venturi;
   a pressure regulator disposed on the housing and fluidly connected to the gas source and being operative to regulate the pressure of gas flowing therefrom;
   an inspiration flow control valve disposed on the housing and interposed between the gas source and the patient, the inspiration flow control valve being operative to open and close in response to patient pressure measurements for producing a desired pressure at the patient;
   a mixture control being configured to allow for selective adjustment of the oxygen concentration delivered to the patient;
   an oxygen mixer connected to the gas source and being operative to deliver a mixture of oxygen and air to the inspiration flow control valve in response to a setting of the mixture control;
   an oxygen sensor operative to measure the oxygen concentration in the gas provided to the patient;
   an exhalation system interconnecting the patient to the gas source and being arranged in parallel with the inspiration flow control valve, the exhalation system being operative to vent exhalation gases from the patient, wherein the exhalation system includes an exhalation valve and an expiratory check valve interconnecting the exhalation valve to the patient, the expiratory check valve being operative to prevent flow in a direction from the exhalation valve to the patient and wherein the exhalation system includes the drive venturi interposed between a voltage sensitive orifice (VSO) valve and the exhalation valve, the drive venturi being operative to facilitate the flow of gas.

17. The pressure driver of claim 16 further comprising a filter connected to the oxygen port and being operative to filter oxygen flowing therefrom.

18. The pressure driver of claim 16 further comprising a battery pack operative to power the pressure driver.

19. The pressure driver of claim 16 further comprising a power supply port mounted on the housing and being connectable to an exterior power source for powering the pressure driver.

20. The pressure driver of claim 16 further comprising:
   a desired patient pressure indicator operative to indicate the desired pressure of gas delivered to the patient;
   an actual patient pressure indicator operative to indicate an actual patient pressure of gas delivered to the patient as measured by the patient pressure sensor.

* * * * *